United States Patent [19]

Bagwell

[11] Patent Number: 4,629,590
[45] Date of Patent: Dec. 16, 1986

[54] NEBULIZER

[75] Inventor: James T. Bagwell, Orange, Calif.

[73] Assignee: CIMCO, Costa Mesa, Calif.

[21] Appl. No.: 661,149

[22] Filed: Oct. 15, 1984

[51] Int. Cl.4 .................. B01F 3/04; A61M 11/02
[52] U.S. Cl. ..................... 261/78.2; 128/200.21;
128/203.27; 215/200; 219/273; 239/338;
261/64.1; 261/142; 261/DIG. 65
[58] Field of Search .............. 261/78 A, 79 A, 123,
261/142, 141, 64 R, DIG. 65, DIG. 77;
239/338; 128/200.18, 200.21, 203.26, 203.27,
202.27, 204.17; 422/228; 55/257 PV, 257 R;
215/200; 220/378; 219/271-276

[56] References Cited

U.S. PATENT DOCUMENTS

| Re. 24,291 | 3/1957 | Goodyer | 261/78 A X |
|---|---|---|---|
| 1,040,801 | 10/1912 | Snyder | 128/203.27 |
| 2,111,841 | 3/1938 | Curry | 239/338 |
| 2,209,261 | 7/1940 | Eicken | 239/338 |
| 2,381,558 | 8/1945 | Robinson | 239/338 |
| 2,432,660 | 12/1947 | Curry | 239/338 X |
| 2,622,593 | 12/1952 | Peirano | 128/203.16 X |
| 2,835,267 | 5/1958 | Andresen et al. | 261/78 A X |
| 2,857,801 | 10/1958 | Murray | 239/338 X |
| 2,890,765 | 6/1959 | Friedell | 261/78 A X |
| 3,077,307 | 2/1963 | Moore et al. | 239/338 |
| 3,206,175 | 9/1965 | Boteler | 239/338 X |
| 3,572,660 | 3/1971 | Mahon et al. | 261/DIG. 65 |
| 3,618,299 | 11/1971 | Vincent | 55/257 PV X |
| 3,659,604 | 5/1972 | Melville et al. | 219/272 X |
| 3,724,454 | 4/1973 | Brown | 261/DIG. 65 |
| 3,779,414 | 12/1973 | Jones | 215/200 X |
| 3,898,429 | 8/1975 | Chodak | 219/307 |
| 4,100,235 | 7/1978 | Thornwald | 128/200.18 X |
| 4,101,611 | 7/1978 | Williams | 261/142 |
| 4,177,945 | 12/1979 | Schwartz et al. | 239/338 |
| 4,201,204 | 5/1980 | Rinne et al. | 128/203.27 |
| 4,203,961 | 5/1980 | Cowley | 422/228 X |
| 4,243,396 | 1/1981 | Cronenberg | 128/203.16 X |
| 4,267,974 | 5/1981 | Kienholz et al. | 128/200.21 X |
| 4,297,563 | 10/1981 | Berry | 219/275 |
| 4,427,004 | 1/1984 | Miller | 128/200.21 |

FOREIGN PATENT DOCUMENTS 22401 of 1906 United Kingdom .

Primary Examiner—Richard L. Chiesa
Attorney, Agent, or Firm—Gausewitz, Carr & Rothenberg

[57] ABSTRACT

A nebulizer providing a moistened breathing mixture for inhalation therapy is arranged to flow a gas-liquid mixture in a circular path around the inner surface of a container that is provided with shallow baffle forming ribs extending vertically across the circular flow path to trap relatively large water particles. A heater is detachably connected to the nebulizer discharge fitting and provides additional structure for trapping and removing larger water particles.

21 Claims, 9 Drawing Figures

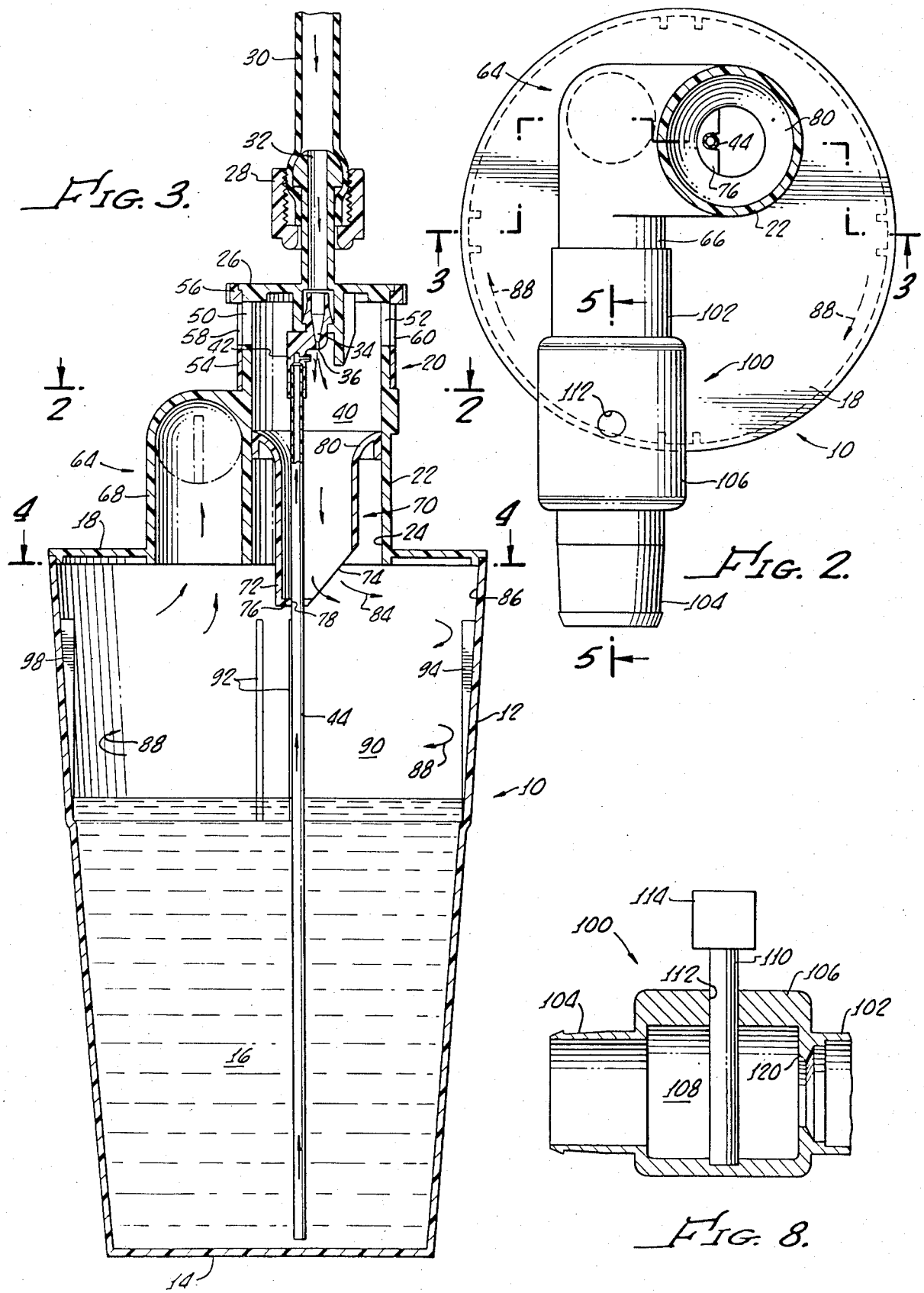

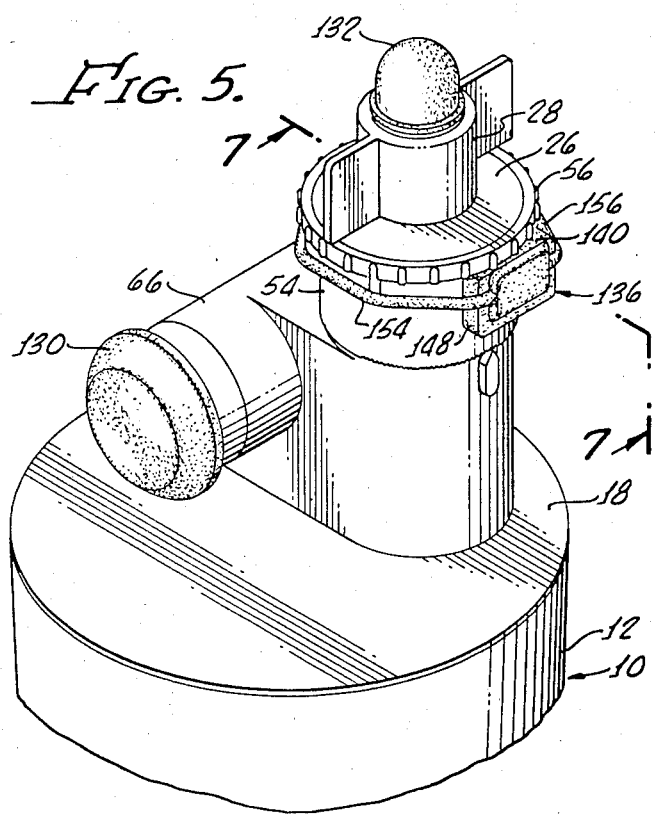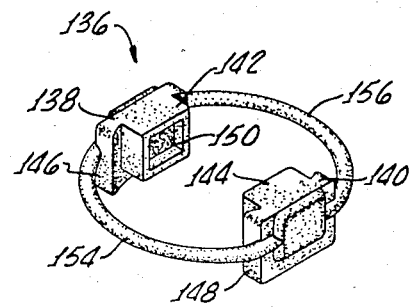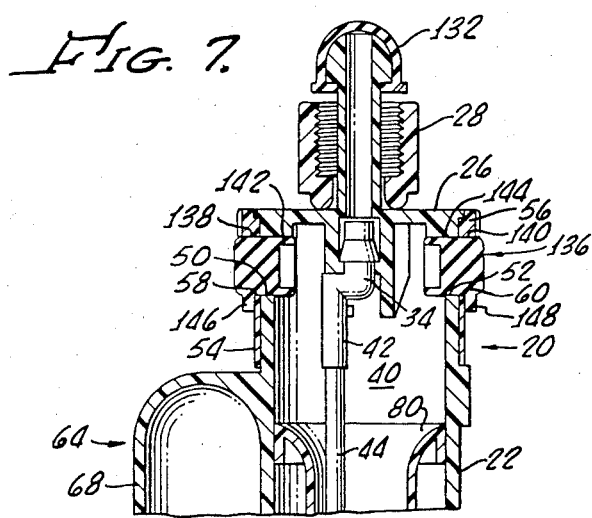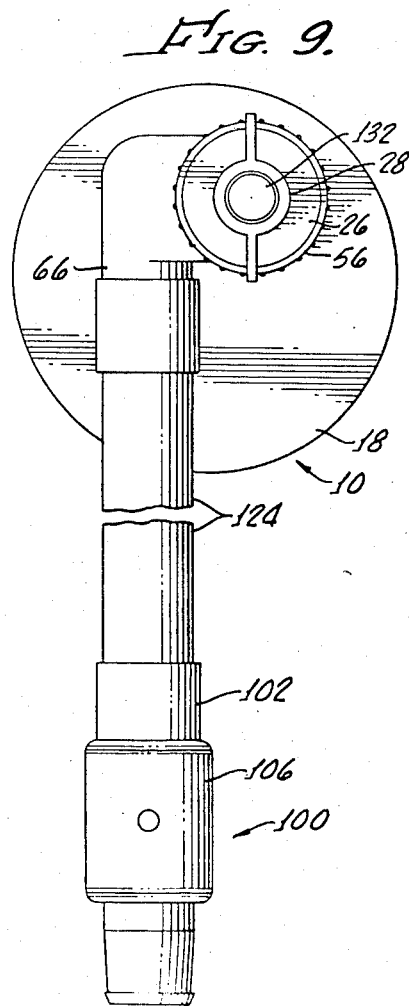

NEBULIZER

BACKGROUND OF THE INVENTION

The present invention relates to nebulizers for inhalation therapy. It more particularly concerns a nebulizer having improved large water droplet removal capability and an improved heating arrangement.

In common forms of inhalation therapy, oxygen or an oxygen enriched mixture of air is provided for introduction to a patient's lungs by means of suitable breathing apparatus. The gas mixture is preferably moisturized and transmitted to the patient through a flexible tube which may be several feet or more in length. Particularly where such a tube is corrugated, but even where it is not, water in the moisturized gas mixture tends to drop out of the mixture, collecting in lower portions or bends of the connecting conduit. The water collected in the conduit may increase in volume to a point where the connecting conduit is either partially or entirely blocked, thereby greatly endangering the patient by obstruction of the supply of breathable gas.

The nebulizer provides a gas stream that entrains water particles rather than water vapor (as in a humidifier). It requires a minimum water particle size because it must insure that water particles will reach deeper portions of the respiratory tract. In a humidifier the gas carries water vapor rather than water particles and the moisture in the inhaled mixture may be absorbed before it reaches deeper portions of the respiratory tract. In the nebulizer, liquid particle size preferably is from about five microns down to about two microns. Particles larger than five microns have a greatly increased tendency to drop out of the mixture during flow from the nebulizer to the patient. It is these large size particles that must be avoided. Thus, large particles in the mixture do no good to the patient because they generally do not remain in the mixture for time long enough to reach the patient. But more importantly, they tend to collect and fully or partially occlude the connecting tubing, requiring frequent attention and draining of the tubing to avoid complete blocking of flow.

Prior attempts to remove larger droplets from the inhalation mixture are basically ineffective, inefficient, complex, and costly. For example, the patent to Cronenberg, U.S. Pat. No. 4,243,396, describes a tortuous spiral path formed between a pair of telescoping tubes as a separator of gas droplets. The patent to Kienholz et al., U.S. Pat. No. 4,267,974, describes a chamber which is termed a baffling chamber having a baffle plate at the chamber exit. The patent to Schwartz al., U.S. Pat. No. 4,177,945, shows a tortuous path that results in turbulent flow for removal of liquid droplets. These arrangements are largely ineffective, greatly complicating nebulizer structure, thereby increasing costs and compromising efficiency.

A nebulizer is employed to provide a gas mixture that will vary from 100% oxygen (less water content) to as little as 28% oxygen. Thus, the nebulizer is provided with an adjustable air intake through which selectively varying amounts of air are admitted to the mixing chamber for mixing with the oxygen that is supplied under pressure. Such air quantity adjusting devices frequently take the form of a sleeve rotatable about an apertured tube with the tube apertures being completely overlapped by the sleeve in the desired 100% oxygen condition. However, the rotatable aperture closing sleeve must be made with tolerances that always result in some space between the sleeve and the tube. This allows some air to be drawn into the mixing chamber even when the adjusting sleeve is in the closed position. Thus with prior nebulizers having an adjustable air intake, it is not possible to achieve the desired 100% oxygen condition.

When the nebulizer involves a heater for controlling temperature of the moisturized breathing mixture, the problem of large droplet fallout is increased, yet the prior art does not recognize or attempt to solve this problem. In the heated mixture, the larger particles are more of a problem because small droplets tend to condense upon the big ones thereby significantly increasing the problem of droplet fallout. Neublizer heaters of the prior art fail to suggest a solution for, or even to recognize, such problem.

Accordingly, it is an object of the present invention to provide a nebulizer that avoids or minimizes the above mentioned disadvantages.

SUMMARY OF THE INVENTION

In carrying out principles of the present invention in accordance with a preferred embodiment thereof, a nebulizer includes a mixing means secured to a liquid container to produce a stream of moisturized gas which is projected into an upper portion of the container so as to flow in a generally horizontal circumferential path around the inner surface of the container. Baffle means are provided on the inner surface extending across the flow path for removing liquid droplets from the stream of gas.

A detachable heater is connected to the nebulizer discharge for flow of the moisturized gas mixture through the heater, thus requiring no modification of the nebulizer, causing the heater to heat only the discharged fluid mixture, and not the nebulizer structure, thereby wasting less heat. In addition, the heater is configured so as to afford additional removal and entrapment of large droplets.

BRIEF DESCRIPTION OF THE DRAWINGS

FIG. 2 is a section taken on line 2—2 of FIG. 3;

FIG. 3 is a section taken on lines 3—3 of FIG. 2;

FIG. 5 is a pictorial view of the upper part of the nebulizer showing the sealing caps in position;

FIG. 6 is a pictorial illustration of the sealing plugs for the air input apertures;

FIG. 7 is a section showing the sealing plugs in position;

FIG. 8 is a sectional view of the heater taken on lines 5—5 of FIG. 2; and

FIG. 9 shows an alternative arrangement of the heater.

DETAILED DESCRIPTION

Figure 1:
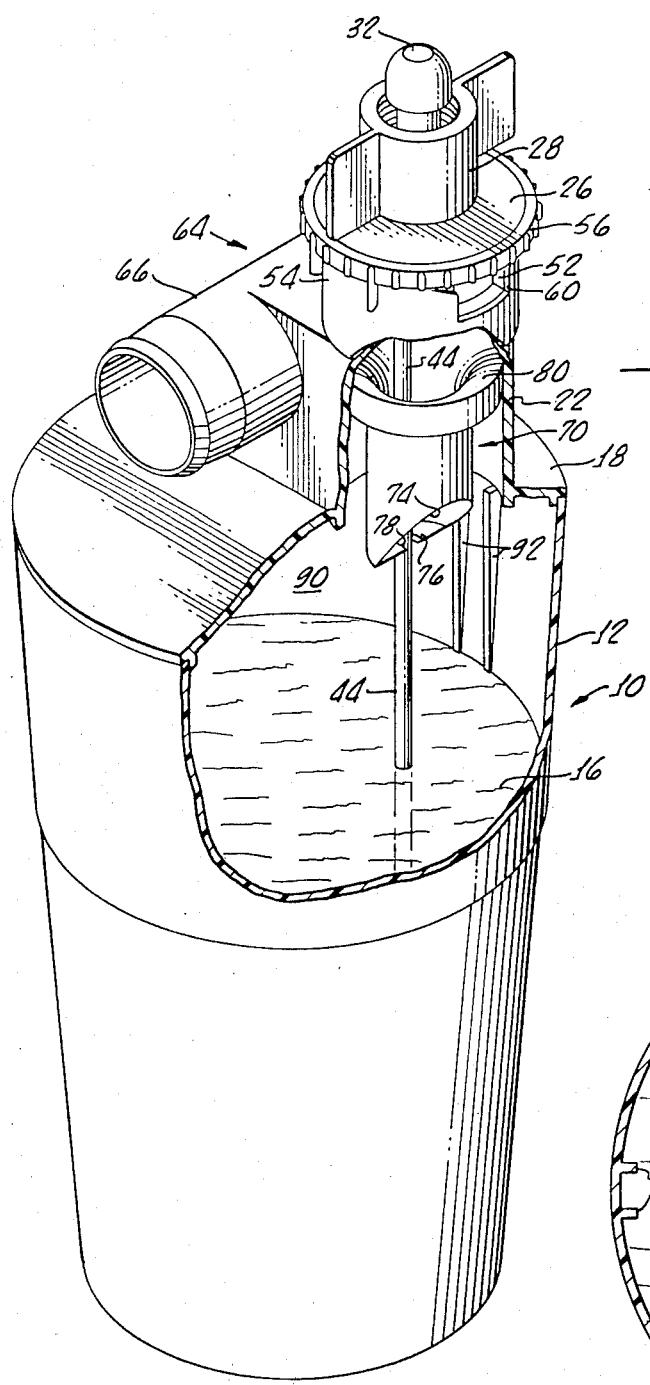
FIG. 1 is a pictorial illustration, with parts broken away, of a unitary nebulizer assembly incorporating features of the present invention.
Figure 4:
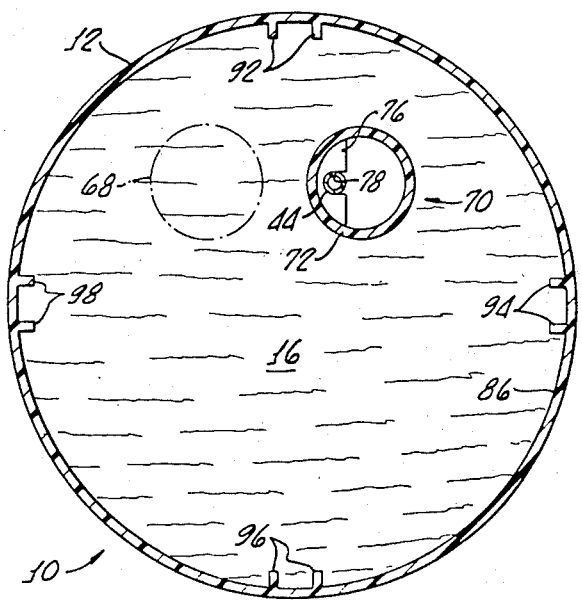
FIG. 4 is a section taken on lines 4—4 of FIG. 3.

Shown in FIGS. 1 and 3 is container 10 having a truncated conical wall 12 and a closed bottom 14 confining a body of liquid, such as water 16, filling the container to a point well below its upper edge. A lid 18 is fixed to and seals the open upper end of the container and is molded integrally with a tubular mixer body 20 including a generally upstanding tubular wall 22 that extends from an opening 24 in the lid upwardly to a body cap 26 to which is secured an input fitting 28 connected to an input oxygen hose 30. Fixed to the cap 26, in line with the input passage 32 of the fitting 28, is a nozzle 34 having a nozzle discharge orifice 36 of decreased diameter, whereby the nozzle will project the incoming gas at high velocity into a mixing chamber 40 defined within the tubular mixer body 22. Mounted to and depending from the cap 26 is a liquid aspirating fitting 42 connected by means of a tube 44 to a lower portion of the container whereby the increased velocity gas projected from nozze orifice 36 will provide a decreased pressure within the tube 44 to draw liquid from the container to be mixed with the projected gas stream. Much of the liquid thus entrained within the increased velocity gas stream is in the form of water droplets, but many such droplets will be larger than the maximum desirable droplet size (about 5 microns).

Tubular body 22 is formed with a pair of outwardly directed apertures 50, 52 that are arranged to be fully or partly closed by an adjustment sleeve 54 having a knurled or serrated operating edge 56 and itself having apertures 58, 60 that will mate with apertures 50, 52 of the tubular body in one position of rotation of sleeve 54. The sleeve may be rotated to progressively decrease the unblocked area of openings 50, 52 so as to adjust the amount of ambient air that will be drawn into the mixing chamber 40 by the decreased pressure provided by the mixture projected from the orifice 36. The mixer body is formed with an elbow conduit 64 having a horizontally directed nebulizer discharge or output leg 66 and a vertically directed leg 68 extending through the lid 18 into communication with the upper portion of container 10.

A mixture venturi tube 70 is fixed within and aligned with the tubular body 22, extending downwardly therefrom in axial alignment with the input passage 32 and the jet nozzle 34, through the lid 18 and terminating at an end 72 below the lid but adjacent the top of the container. Part of the wall of venturi tube 70 is cut away at the tube bottom as indicated at 74 to provide a laterally directed opening at the lower end of the venturi tube. This end of the venturi tube is partially blocked by a horizontal deflector plate 76 which is formed with a circular recess 78 through which extends the tube 44 for passage of liquid from the container to the mixing chamber 40. As can be seen in FIG. 3, tube 44 is offset slightly to the side of the nozzle orifice 36 so that the gas stream projected at increased velocity from the nozzle orifice will travel downwardly, expanding as it travels to impinge upon an upper curved entrance portion 80 of the venturi tube. The high velocity jet mixture is funneled by the venturi tube downwardly to its open end to impinge upon deflector 76 which redirects the jet stream outwardly from a point within the container at its upper portion, as indicated by arrows 84, to impinge upon the inner surface 86 of the container wall at an angle to the surface of this wall. The angular impingement of the redirected mixture upon the container wall again deflects the projected stream, redirecting the stream to flow circumferentially, in a generally horizontal plane, around the interior surface of the container 12 in the directions indicated by arrows 88 (FIG. 2).

The upper portion of container 12 between the lid and the upper surface of the liquid 16 defines a swirl chamber 90 into which the moisture entraining high velocity stream of oxygen or oxygen enriched air is projected. The mixture is projected outwardly from a point within the swirl chamber and caused to flow in the described circumferential and substantially horizontal path. The mixture may begin to descend along the container walls in a downward spiral path as it swirls around the walls. Fixed to the inner surface of container wall 12 is a plurality of circumferentially spaced baffles 92, 94, 96 and 98 each of which extends vertically along the container sides. The baffles, in effect, form stiffening ribs for the container wall, but, because of their vertical extent across the horizontal direction of swirling mixture flow, primarily provide limited obstructions or obstacles to the circumferential flow of the mixture. Large water droplets entrained in the swirling gas mixture impinge upon the baffles in the course of the swirling flow of the mixture and are trapped, thereby to be removed from the swirling mixture and to flow downwardly along the container sides into the body of water within the container.

The pressurized swirling mixture from the chamber 90 flows outwardly to be discharged from the container through discharge conduit 64.

As shown in FIGS. 2 and 8, a detachable and disposable heater 100 has an input fitting 102 connected to output leg 66 of the discharge conduit 64 and has a heater output fitting 104. The heater includes an intermediate enlarged body portion 106 forming an enlarged heater chamber 108 between the input and output fittings 102, 104. A cylindrical heater element 110, mounted to the heater body, extends through an aperture 112 in the enlarged heater section 106 and terminates in an electrical connector 114 to which may be connected suitable power wires for the heater element and sensing wires for a thermocouple contained within the heater element 110. An annular heater baffle 120 projects radially inwardly from the interior surface of heater input fitting 102 at the junction of this fitting with the intermediate heater section 106. Heater chamber 108 has an increased diameter, being larger in cross-sectional area than the cross-sectional area of the input of the heater input fitting 102, and therefore, larger than the area of the passage through the heater baffle 120.

The illustrated heater configuration acts to further entrap water droplets and remove such large water droplets from the inhalation mixture. Baffle 120 acts to decrease the passage area, thus increasing its velocity. The baffle causes further entrapment of relatively large water particles which may then flow into the enlarged heater chamber 108. The flowing mixture passing through the enlarged heater chamber 108 decreases in velocity, thus providing a greater time for the desired heat exchange between the heater element and the mixture. In addition, the heater element raises the temperature of water that may collect in the bottom of the heater chamber, thus vaporizing water in the bottom of the heater chamber which then is again entrained as the desirably small sized droplets or vapor within the flowing mixture. The moisturized mixture having been heated in the heater chamber and further cleansed of larger water droplets, now may flow through the heater output fitting 104 and thence through an inhalation conduit (not shown) attached to the fitting 104 and connected to suitable breathing apparatus of the subject of the inhalation therapy.

If necessary or desirable, the heater 100 may be physically separated from the nebulizer as shown in FIG. 9 by attaching the heater input fitting 102 to a relatively short section of connecting tubing 124 which itself is connected to the output leg 66 of the nebulizer discharge fitting. With this arrangement, the heater is located closer to the patient and thus, there is less heat loss between the heater and the patient. Moreover, the heater need not waste any of its energy in heating any of the mass of the nebulizer container or mixer body itself and thus, the heater may be more efficiently employed for its intended purpose while at same time maintaining a desirably lower temperature of the nebulizer container. Displacement of the heater from the container allows the container to be made of a plastic or material that might be adversely affected by a temperature increase caused by proximity to the heater.

Preferably, the heater adapter is disposable and removably attachable to the nebulizer and thus the nebulizer construction and configuration need not be modified for the heater. The heater may be applied to nebulizers of many different constructions and the nebulizer itself need not be specially formed or structured for acceptance of the heater. The mixture is heated after it has completely passed through the nebulizer and is thus less subject to other temperature changes thereby to afford better control of output mixture temperature. Still further as previously mentioned, the heater itself is configured to further remove the larger water droplets, with the collected water droplets being vaporized within the heater chamber to mix the small droplets with the exiting mixture.

An unusual, surprising, and totally unexpected advantage of the described configuration is its quiet operation. Prior art nebulizer generate a significant amount of sound, which appears to emanate from the discharge tube. This sound is transmitted through the conduit connecting to the patient. It is found that the operation of the nebulizer described herein is as much as 50% quieter than commonly used prior art nebulizers. It is postulated that the significant decrease in noise of operation is due to the discharge of the liquid entraining mixture into the relatively large swirling chamber 90 and the structure of the nebulizer which directs this discharge into a relatively large diameter swirling path.

Preferably the container 10 is made as a one-piece molded vessel with the baffles 92 through 98 being tapered as illustrated in FIG. 3 solely for ease of molding. Lid 18 together with mixer body 20 are also molded as a single integral unit to which is then affixed to the jet nozzle 34, the aspirator 42, tube 44 connected between the aspirator and the container bottom and the air adjustment sleeve 54. All parts are sterilized. Sterile water is introduced into the container to a suitable level below the container top (which may be one or two inches below the top) for an exemplary container that may be six inches from lid to bottom and three and a half inches in diameter at its lid.

As illustrated in FIG. 5, the nebulizer is filled with sterile water and fully sealed for shipping. The sealing arrangement includes a removable resilient sealing cap 130 that is secured to an outlet conduit leg 66 and a removable resilient sealing cap 132 which is secure to the input fitting 28 that receives the input oxygen hose 30. In addition to the oxygen input and mixture discharge outputs of the nebulizer, the adjustable air intake apertures 50, 52, of the mixer body 20 must be sealed. Although the sleeve 54 may be rotated to a position where no part of the apertures 50 and 52 overlap the sleeve apertures 58, 60 so that the nebulizer apertures 50, 52, supposedly are fully closed, a full 100% sealing of these apertures by the sleeve 54 is not possible on a practical device. Accordingly, even if the sleeve 54 is moved to its fully closed position, there still is some space between the sleeve and the tube 22 through which external air could be admitted to the interior of the nebulizer. For this reason, to completely seal the nebulizer for handling and shipping, a unitary sealing plug assembly 135 (see FIGS. 5 and 6) is provided. The plug assembly has sealing plugs 138, 146 each having a solid plug body 142, 144 having a shape and a size closely mating with the shape and size of the respective aperture 50, 52 and each having an outwardly extending flange 146, 148 encircling three sides of the plug body 142, 144 respectively. Plug bodies 142, 144 are each recessed, as at 150 for plug 138, to provide increased flexibility of the plug and decreased material. The two plugs are interconnected by resilient bands 154, 156 to complete a continuous unbroken circular plug assembly. The entire assembly is molded as a unitary article of a suitable resilient plastic and configured so that the bands 154, 156 are in tension when the plug assembly is installed in its sealing relation. Thus, the resilience of the bands 154, 156 tightly hold the plugs in sealing relation to and within the air input openings 50, 52, (and also extending through apertures 58, 60 of adjustment sleeve 54) and yet they may easily be removed as desired by further stretching of the resilient bands.

An unexpected and surprising result of the use of the sealing assembly 136 to seal the nebulizer for packaging and handling is the fact that the nebulizer is capable of providing a true 100% oxygen gas when it is operated with the sealing assembly 136 in place. Of course, in such operation the sealing caps 130, 132 are removed and appropriate connections made to input and output fittings. With the sealing assembly 136 in place, the nebulizer may be operated to provide 100% oxygen and it is not necessary to rely on the adjusting sleeve 54 for total blockage of apertures 50, 52. Thus the sealing plugs 138, 140 provide a dual function. First, they seal the mixer body openings during handling and shipping to prevent loss of liquid and to maintain sterility. Second, they may be inserted in apertures 50, 52 when the nebulizer is in use, to thereby fully and completely seal these apertures to ensure a true 100% oxygen flow, when needed.

I claim:

1. A nebulizer for producing a stream of moisturized gas for inhalation therapy, said nebulizer comprising

- a container having a circular wall for confining a quantity of liquid,
- a mixing body connected to an upper part of said container and having a discharge port communicating with the interior of said container,
- means in said mixing body for projecting a stream of gas into the interior of the container through said discharge port,
- means in said mixing body for drawing liquid from said container and mixing such liquid with said stream of gas within said mixing body to provide a stream of moisturized gas projected along an axis laterally offset from the center of said container,
- means for directing said projected stream of moisturized gas at an acute angle to the surface of the container wall so as to be redirected to flow circumferentially in a swirling path extending around the container,
- baffle means at the container wall extending vertically across said path for separation of liquid droplets from said stream of gas, and
- output port means for discharging moisturized gas from said container.

2. The nebulizer of claim 1 wherein said swirling path extends substantially horizontally around the inner surface of said container, said baffle means comprising a plurality of mutually spaced vertically extending ribs fixed to said container inner surface and projecting a small distance toward the interior of the container.

3. The nebulizer of claim 1 wherein said mixing body includes a venturi tube extending therefrom and having an end positioned within said upper part of said container, said venturi tube end comprising said discharge port, said means for directing said projected stream of moisturized gas comprising deflecting means on the end of said venturi tube for changing direction of a stream of gas flowing through said discharge port.

4. The nebulizer of claim 3 wherein said venturi tube projects downwardly into said upper part of said container and has an opening in an end portion thereof, said opening extending across the end of said venturi tube and upwardly along one side thereof, said deflecting means comprising a member extending partly across said tube to partially block said opening in the tube end.

5. A nebulizer for producing a stream of moisturized gas for inhalation therapy comprising a closed container having a liquid in a lower portion and having a circular upper portion above the liquid, mixing means secured to said container for producing a stream comprising a mixture of gas having liquid from said container lower portion entrained therein, means for projecting said stream at an acute angle to the upper portion of said container so as to flow in a generally horizontal circumferential swirling path around the inner surface of said upper portion, elongated substantially vertically extending baffle means on said inner surface extending across said path for removing liquid droplets from said stream, and means for discharging said mixture from said container.

6. The nebulizer of claim 5 wherein said baffle means comprises a plurality of circumferentially spaced vertically extending ribs fixed to said container inner surface and projecting slightly inwardly from said inner surface.

7. The nebulizer of claim 6 wherein said container comprises a vessel having an open top, wherein said mixing means comprises a lid secured to and sealing the top of said vessel, a mixer body mounted to said lid and defining a mixing chamber therein, said mixer body having a gas input port communicating with said mixing chamber, and wherein said means for projecting said stream comprises a venturi tube mounted in said mixer body and extending through said lid into said container upper portion, and nozzle means in said mixer body for projecting gas from said input port through said venturi tube.

8. The nebulizer of claim 7 including a deflector fixed to an end of said venturi tube.

9. The nebulizer of claim 8 wherein said container, said lid and said mixer body are fixedly assembled to one another and sealed together with a quantity of liquid in the container to provide a unitized and sanitized assembly of mixer, liquid and container all pre-packaged and ready for use without further assembly.

10. The nebulizer of claim 8 wherein said means for discharging said mixture comprises an output fitting on said lid in fluid communication with the interior of said vessel, and including a heater detachably coupled to said output fitting for passing and heating mixture that is discharged from said interior.

11. A nebulizer for producing a stream of moisturized gas for inhalation therapy comprising a closed container having a liquid in a lower portion and having a circular upper portion above the liquid, mixing means secured to said container for producing a stream comprising a mixture of gas having liquid from said container lower portion entrained therein, means for projecting said stream at an angle to the upper portion of said container so as to flow in a generally horizontal circumferential path around the inner surface of said upper portion, baffle means on said inner surface extending across said path for removing liquid droplets from said stream, said baffle means comprising a plurality of circumferentially spaced vertically extending ribs fixed to said container inner surface and projecting slightly inwardly from said inner surface, means for discharging said mixture from said container, said container comprising a vessel having an open top, said mixing means comprising a lid secured to and sealing the top of said vessel, a mixer body mounted to said lid and defining a mixing chamber therein, said mixer body having a gas input port communicating with said mixing chamber, said means for projecting said stream comprising a venturi tube mounted in said mixer body and extending through said lid into said container upper portion, and nozzle means in said mixer body for projecting gas from said input port through said venturi tube, said venturi tube having a generally vertical axis, extending downwardly from said lid and having an end portion positioned in said container upper portion, said venturi tube end portion having an opening extending for a distance along a side of the tube from the tube end, and a deflector fixed to the tube and extending at an angle to the tube axis.

12. A nebulizer for producing a stream of moisturized gas for inhalation therapy comprising a closed container having a liquid in a lower portion and having a circular upper portion above the liquid, mixing means secured to said container for producing a stream comprising a mixture of gas having liquid from said container lower portion entrained therein, means for projecting said stream at an angle to the upper portion of said container so as to flow in a generally horizontal circumferential path around the inner surface of said upper portion, baffle means on said inner surface extending across said path for removing liquid droplets from said stream, said baffle means comprising a plurality of circumferentially spaced vertically extending ribs fixed to said container inner surface and projecting slightly inwardly from said inner surface, means for discharging said mixture from said container, said container comprising a vessel having an open top, said mixing means comprising a lid secured to and sealing the top of said vessel, a mixer body mounted to said lid and defining a mixing chamber therein, said mixer body having a gas input port communicating with said mixing chamber, said means for projecting said stream comprising a venturi tube mounted in said mixer body and extending through said lid into said container upper portion, and nozzle means in said mixer body for projecting gas from said input port through said venturi tube, said container, said lid and said mixer body being fixedly assembled to one another and sealed together with a quantity of liquid in the container to provide a unitized and sanitized assembly of mixer, liquid and container all pre-packaged and ready for use without further assembly, said mixer body including an air admitting aperture, an apertured sleeve adjustably mounted on said body and having a sleeve aperture for variably opening or blocking said air admitting aperture, said sleeve being incapable of completely blocking said air admitting aperture, a sealing plug extending through both said apertures and completely sealing said air admitting aperture, and means for holding said sealing plug in and sealed to said air admitting aperture, whereby said sealing plug can be used to seal said air admitting aperture for handling and shipping of said nebulizer and can also be used to seal said air admitting aperture during use of the nebulizer to provide air free oxygen for inhalation therapy.

13. A nebulizer for producing a stream of moisturized gas for inhalation therapy comprising a closed container having a liquid in a lower portion and having a circular upper portion above the liquid, mixing means secured to said container for producing a stream comprising a mixture of gas having liquid from said container lower portion entrained therein, means for projecting said stream at an angle to the upper portion of said container so as to flow in a generally horizontal circumferential swirling path around the inner surface of said upper portion, baffle means on said inner surface extending across said path for removing liquid droplets from said stream, means for discharging said mixture from said container, said means for discharging said mixture comprising an output fitting on said lid in fluid communication with the interior of said vessel, and including a heater detachably coupled to said output fitting for passing and heating said mixture that is discharged from said interior, said heater comprising input and output heater fittings and a heater chamber between said heater fittings, said heater chamber having a cross sectional area greater than the cross sectional area of said input heater fitting, whereby the velocity of mixture flowing from said input heater fitting to said chamber decreases in said chamber, said heater input fitting having means for trapping liquid droplets, and a heater mounted in said heater chamber.

14. The nebulizer of claim 13 wherein said means for trapping liquid droplets comprises heater baffle means in said heater input fitting.

15. A nebulizer for producing a stream of a mixture of gas and liquid for inhalation therapy comprising a container confining a body of liquid, mixing means connected with said container for mixing gas with liquid in said container, a discharge fitting connected with said container for discharging a liquid gas mixture from the container, and a heater detachably connected with said discharge fitting, said heater comprising a heater input fitting adapted to be connected to said discharge fitting, a heater output fitting adapted to be coupled to an inhalation therapy conduit, a heater chamber connected to and between said heater input and output fittings, said heater comprising a unitary heater body having an enlarged intermediate section forming said heater chamber, said heater input fitting comprising a first end section of said body having an input bore, comprising a second end portion of said heater body having an output bore, a heater element mounted within said heater chamber, and baffle means in said heater body adjacent said heater input fitting for trapping liquid particles, said heater chamber adapted to collect trapped liquid particles, said mixture passing through said relatively larger heater chamber to said heater output fitting with a decreased velocity thereby to enhance vaporization of liquid particles collected in said heater chamber.

16. A nebulizer comprising an upright container having a body of liquid confined in a lower portion thereof and having an open top, a lid sealed to and closing the top of said container, a mixer body fixed to said lid above the container, said mixer body having an input fitting adapted to receive pressurized gas, a nozzle connected to said input fitting for projecting a stream of said gas of increased velocity, means for aspirating liquid from said container into said stream of gas to provide a moisturized stream of gas of increased velocity, a venturi tube mounted to said mixer body and having an end portion projecting through said lid into an upper portion of said container, said venturi tube being positioned to receive and guide a moisturized stream of increased velocity gas projected from said nozzle, said venturi tube including means for directing said moisturized stream of increased velocity gas in a generally horizontal direction and at an angle to an inner surface of the upper portion of said container, whereby said moisturized stream of gas is deflected by said container inner surface to flow in a circumferential path about the interior of the container, a plurality of mutually spaced vertically extending ribs fixed to and positioned circumferentially around the inner surface of said container upper portion for obstructing circumferential flow of said moisturized stream of gas around said container to thereby trap liquid particles, and means for discharging moisturized gas from the interior of said container.

17. A nebulizer for producing a stream of moisturized gas for inhalation therapy comprising a container for confining a quantity of liquid, mixing means secured to said container for providing a stream comprising a mixture of gas having liquid from said container entrained therein, said mixing means having a plurality of apertures including an input port adapted to receive a flow of oxygen, and an air admitting aperture for receiving ambient air to be mixed with said oxygen in said mixing means, adjusting means for adjustably closing said air admitting aperture, a removable sealing plug positioned in said air admitting aperture for completely sealing said aperture, whereby said nebulizer may be completely sealed by sealing said plurality of apertures in the nebulizer, and whereby said nebulizer may be operated with said air admitting aperture completely sealed to provide a flow of moisturized oxygen that is free of air, and means for maintaining said sealing plug in said air admitting aperture comprising an elastic ring secured to said plug and extending around said mixer body.

18. The nebulizer of claim 17 wherein said sealing plug includes a body portion precisely conforming to the size and shape of said air admitting aperture and a flange portion fixed to said body portion and extending laterally from the body portion along the exterior surface of said mixing means when said plug is inserted in said air admitting aperture, said flange portion having an inner surface comforming precisely to the shape of a portion of said mixing means adjacent said air admitting aperture.

19. The nebulizer of claim 18 wherein said mixing means includes a second air admitting aperture oppositely disposed on said mixing means with respect to the first mentioned air admitting aperture, a second plug seated in and sealing said second air admitting aperture, and first and second resilient elastic members interconnecting said sealing plugs to form a continuous plug assembly encircling said mixing body.

20. A nebulizer comprising an upright container having a body of liquid confined in a lower portion thereof and having an open top, a lid closing the top of said container, a mixer body fixed to said lid above the container, said mixer body having an input fitting adapted to receive pressurized gas, a nozzle connected to said input fitting for projecting a stream of said gas of increased velocity, means for aspirating liquid from said container into said stream of gas to provide a moisturized stream of gas of increased velocity, a venturi tube mounted to said mixer body and having an end portion projecting into an upper portion of said container, said venturi tube being positioned to receive and guide said moisturized stream of increased velocity gas projected from said nozzle, means for directing said moisturized stream of increased velocity gas from said venturi tube in a generally horizontal direction along a line offset from the center of said container and at an acute angle to an inner surface of the upper portion of said container, whereby said moisturized stream of gas is deflected by said container inner surface to flow in a circumferential path about the interior of the container, a plurality of vertically extending baffles positioned circumferentially around the inner surface of said container upper portion of obstructing circumferential flow of said moisturized stream of gas around said container to thereby trap liquid particles, and means for discharging moisturized gas from the interior of said container.

21. A nebulizer for producing a stream of a mixture of gas and liquid for inhalation therapy comprising a container confining a body of liquid, mixing means connected with said container for mixing gas with liquid in said container, a discharge fitting connected with said container for discharging a liquid gas mixture from the container, and heater means detachably connected with said discharge fitting for heating the discharged mixture and removing liquid droplets therefrom, said heater means comprising, a heater input fitting adapted to be connected to said discharge fitting, a heater output fitting adapted to be coupled to an inhalation therapy conduit, a heater chamber connected to and between said heater input and output fittings, and having a diameter greater than the diameter of said heater input fitting to cause decreased velocity of said mixture and increased removal of liquid droplets in said chamber means for increasing velocity of the mixture entering said heater chamber and for trapping liquid droplets, said last mentioned means comprising baffle means at said input fitting for decreasing the effective area of said input fitting, and means for heating a gas-liquid mixture within said heater chamber.

* * * * *